Figure 1:
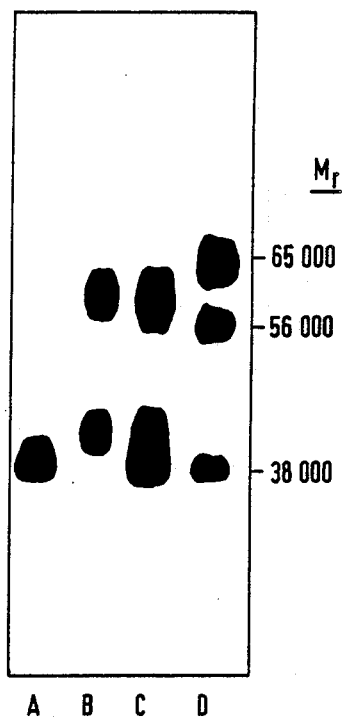

United States Patent [19]

Dodd

[11] Patent Number: 4,970,159
[45] Date of Patent: Nov. 13, 1990

[54] HUMAN TISSUE PLASMINOGEN ACTIVATOR CONSISTING ESSENTIALLY OF T-PA RESIDUES 160 TO 527

[75] Inventor: Ian Dodd, Buckland, England

[73] Assignee: Beecham Group p.l.c., England

[21] Appl. No.: 846,903

[22] Filed: Apr. 1, 1986

[30] Foreign Application Priority Data

Apr. 3, 1985 [GB] United Kingdom ............... 8508717

[51] Int. Cl.$^5$ ..................... C12N 9/48; C12N 9/64
[52] U.S. Cl. ............................ 435/226; 435/212
[58] Field of Search ............ 435/212, 215, 217, 226, 435/172.3; 424/94.64; 935/14, 10

[56] References Cited

FOREIGN PATENT DOCUMENTS 234051 9/1987 European Pat. Off. ............ 435/226

OTHER PUBLICATIONS

Dodd et al., *Thrombosis and Haemostasis*, vol. 59(3), 523-528 (1988).
Browne et al., *Thrombosis and Haemostasis*, vol. 54(2), 422-424 (1985).
Elaine Lynette Wilson et al., Cancer Research, 40, 933 (1980).
Pennica, D. et al (1983), Nature, 301, 214-221.
Rijken, D. C. (1984), Haemostasis, 14, 14.
Huessen, C. and Dowdle, E. B. (1980), Anal. Biochem., 102, 196-202.
Gilbert, L. C. and Wachsman, J. T. (1982), Biochim. Biophys. Acta., 704, 450-460.
Sueishi, K. et al. (1982) Biochim. Biophys. Acta., 717, 327-336.
Ny, T. et al. (1984), Proc. Natl. Acad. Sci., U.S.A., 81, 5355.
Korninger et al., Thromb. Haemostas (Stuttgart), 46(3), 658-661 (1981).
Rijken, D. et al. *J. Biolog. Chem.*, vol. 256, pp. 7035-7041 (1981).
van Zonneveld et al. *Proc. Natl. Acad. Sci.*, vol. 83, pp. 4670-4674 (Jul. 1986).
Kagitani, H., et al. *FEBS*, vol. 189, pp. 145-149 (Sep. 1985).
Browne, M. et al. *Gene*, vol. 33, pp. 279-284 (1985).
Rijken, D. et al. *J. Biol. Chem.*, vol. 261, pp. 3098-3102, (Mar. 1986).
van Zonneveld et al. Thrombosis and Haemostasis, vol. 54, Jul. 15, 1985, Abstract 022.
Pannekoek, EMBO Workshop on Plasminogen Activation, Amalfi, Italy, Oct. 14-18, 1985.
Kluft et al. Text of paper presented at EMBO Workshop on Plasminogen Activation, Amalfi, Italy, Oct. 14-18, 1985.

*Primary Examiner*—Richard A. Schwartz
*Assistant Examiner*—Larry Millstein
*Attorney, Agent, or Firm*—Jacobs & Jacobs

[57] ABSTRACT

A purified fibrinolytically active degraded species of tissue-type plasminogen activator comprising a fibrinolytically intact B chain of native t-PA linked to kringle 2 as the only functionally and structurally intact domain of native t-PA A chain.

5 Claims, 2 Drawing Sheets

HUMAN TISSUE PLASMINOGEN ACTIVATOR CONSISTING ESSENTIALLY OF T-PA RESIDUES 160 TO 527

The present invention relates to a degraded species of an enzyme, the isolation of that species, pharmaceutical compositions containing that species and its use in the treatment of thrombotic disease.

The human fibrinolytic enzyme, tissue-type plasminogen activator (t-PA), has been used in the treatment of thrombosis. However, a disadvantage of this enzyme is that its activity disappears rapidly in-vivo due to clearance via the liver and inactivation by natural antiproteases.

Irreversible blocking of the active site of native t-PA has little effect on the rapid clearance of the t-PA molecule; it was, therefore, suggested that reversible blocking of the active site of t-PA with active site titrants such as p-anisic acid would not prolong its biological half-life (Korninger, C. et al, 1981, Thromb Haem., 46, 658–661).

Native human t-PA exists in two forms, of molecular weight ($M_r$) = 63,000 and 65,000 (Pennica, D. et al, 1983, Nature, 301, 214–221). Apart from the isolated active light chain of t-PA (Rijken, D. C., 1984, Haemostasis, 14, 14;) two fibrinolytically-active degraded species of t-PA have been described previously: $M_r$ = approx. 55,000 (Wilson, E. L. et al, 1980 Cancer Res., 40, 933–938; Huessen, C. and Dowdle, E. B., 1980, Anal. Biochem, 102, 196–202; Gilbert, L. C. and Wachsman, J. T., 1982, Biochim. Biophys. Acta., 704, 450–460; Sueishi, K. et al, 1982. Biochim Biophys. Acta., 717, 327–336) and $M_r$ = approx. 38,000 (Wilson, E. L. et al, 1980; Gilbert, L. C. and Wachsman, J. T., 1982). However, neither have been isolated and characterised.

Unlike native t-PA the $M_r$ = 55,000 species of t-PA is reported not to bind strongly to a fibrin clot (Banyai, L. et al, 1983, FEBS, 163, 37–41). It is not unreasonable to assume that the $M_r$ = 38,000/40,000 species of t-PA should have lost at least the same part of the native t-PA enzyme as that lost by the $M_r$ = 55,000 species. Therefore the $M_r$ = 38,000/40,000 species would not be expected to show fibrin affinity Surprisingly, the applicants have found that the $M_r$ = 38,000/40,000 species of t-PA retains significant affinity for a human fibrin clot. In addition it has surprisingly been found that forms of the $M_r$ = 38,000/40,000 species have reduced clearance rates in-vivo.

The $M_r$ = 38,000/40,000 species has been sequenced and found to comprise the N-terminal sequence Alanine-glycine-lysine-tyrosine-. This may be compared with the sequence for native t-PA described by Pennica et al. from which it can be deduced that the N-terminal amino acid residue of the species corresponds to residue 160 of native t-PA. The species will hereinafter be designated alanine $_{160}$t-PA (ala$_{160}$-t-PA).

Native t-PA is composed of a light (B) and a heavy (A) chain. The B chain contains the active site of the enzyme. It has been shown (Ny, T. et al, 1984, Proc. Natl Acad. Sci. USA 81, 5355, "The structure of the human tissue-type plasminogen activator gene: Correlation of intron and exon structures to functional and structural domains") that the A chain exhibits a number of structural and functional domains which are homologous to structures found in other plasma proteins two triple disulphide bonded structures or kringles, a growth-factor-like domain and a fibronectin-finger-like domain. The t-PA molecule may therefore be described in terms of these domains as FGK1K2B, where F is the finger domain, G is the growth factor domain, K1 and K2 are the kringle structures and B is the B chain.

The ala$_{160}$-t-PA species consists essentially of the B chain of native t-PA together with kringle 2 (K2); the residue ala$_{160}$ is located within kringle 1 such that in the ala$_{160}$-t-PA species, insufficient amino acid residues of kringle 1 are present to provide structural and functional integrity for that domain.

The preparation of a genetically engineered t-PA mutein consisting of B chain and kringle 2 has been described previously (Netherlands Red Cross Blood Transfusion Service, EMBO workshop on Plasminogen Activation, Amalfi, Italy Oct. 14–18, 1985, and the Xth International Congress on Thrombosis and Haemostasis, U.S.A., July 14–19, 1985. However the isolation and purification of the material has not been described.

According to the present invention there is provided a purified fibrinolytically active degraded species of tissue-type plasminogen activator comprising a fibrinolytically intact B chain of native t-PA linked to kringle 2 as the only functionally and structurally intact domain of native t-PA A chain.

Suitably the degraded species is at least 70% pure when measured by a conventional method such as sodium dodecylsulphate polyacrylamide gel electrophoresis.

Preferably the degraded species is at least 80% pure and more preferably at least 95% pure.

In one preferred aspect, the degraded species is ala$_{160}$-t-PA.

In another preferred aspect, the degraded species has a molecular weight in the region of 38,000–40,000.

The invention further provides a method for the preparation of a degraded species of t-PA as herein defined, which method comprises expressing DNA encoding said degraded species in a recombinant host cell and recovering the degraded t-PA product.

The method of the invention may be performed by conventional recombinant techniques such as described in Maniatis et. al., Molecular cloning—A Laboratory Manual; Cold Spring Harbor, 1982.

In a preferred aspect, the substantially pure form of the ala$_{160}$-t-PA or $M_r$ = 38,000–40,000 species can be obtained by separation from native t-PA obtained from a t-PA-secreting cell line, for example using chromatography.

Preferably the native t-PA employed in the separation process is partially purified (for example as described in M. J. Browne et al, 1985, Gene 33,279).

The chromatography may be carried out using an appropriate molecular weight sieve for example Sephadex.

Preferably at least two chromatography steps are employed Concentration for example by means of ultrafiltration is preferably effected after each chromatography step.

It has been found that the degraded species termed $M_r$ = 38,000/40,000 may be separated into two variants of $M_r$ = 38,000 and $M_r$ = 40,000, probably differing only in a carbohydrate group on the amino acid residue asparagine 184, by analogy with the two variants of native t-PA ($M_r$ = 63,000 and 65,000) which differ in this way (ref. 08 Pohl, G. et al, Biochemistry 1984, 23, 3701-7).

In a further preferred aspect, the degraded species has a molecular weight of around 38,000.

The degraded species of t-PA of the invention may be derivatised to provide pharmaceutically useful conjugates analogous to known t-PA-containing conjugates, for example:

(a) an enzyme-protein conjugate as disclosed in EP-A-O 155 388, in which the catalytic site on the enzyme which is responsible for fibrinolytic activity is blocked by a human protein attached thereto by way of a reversible linking group;

(b) an enzyme-protein conjugate as disclosed in EP-A-O 152,736, comprising at least one optionally blocked fibrinolytic enzyme linked by way of a site other than the catalytic site responsible for fibrinolytic activity to at least one human protein;

(c) a protein-polymer conjugate as disclosed in co-pending U.S. application Ser. No. 802,663, filed Nov. 27, 1985 comprising a pharmaceutically useful protein linked to at least one water soluble polymer by means of a reversible linking group; or (d) an enzyme conjugate as disclosed in co-pending U.S. application Ser. No. 802,664, filed Nov.27, 1985 comprising a plurality of fibrinolytic enzymes linked together through the active centers thereof by means of a removable blocking group.

The degraded species of t-PA of the invention may take the place of t-PA as the enzyme or (human) protein component, as appropriate, of any of the conjugates described above.

The degraded species of t-PA or conjugate thereof can be further derivatised such that any catalytic site essential for fibrinolytic activity is optionally blocked by a removable blocking group.

It has been found that reversible blocking of the active site of the ala$_{160}$-t-PA species or the $M_r$=38,000/40,000 t-PA species results in slower clearance rates in-vivo.

Therefore, further according to the invention there is provided a fibrinolytically active degraded species of tissue-type plasminogen activator as defined, wherein the catalytic site essential for fibrinolytic activity is blocked by a removable blocking group.

As used herein the expression 'removable blocking group' includes groups which are removable by hydrolysis at a rate such that the pseudo-first order rate constant for hydrolysis is in the range of $10^{-6}$ sec$^{-1}$ to $10^{-2}$ sec$^{-1}$, preferably $10^{-3}$ sec$^{-1}$ to $10^{-5}$ sec$^{-1}$ in isotonic aqueous media at pH 7.4 at 37° C.

Such blocking groups are described in European Patent No. 0009879 and include acyl groups such as optionally substituted benzoyl or optionally substituted acryloyl.

Suitable optional substituents for benzoyl blocking groups included halogen, $C_{1-6}$ alkyl, $C_{1-6}$ alkoxy, $C_{1-6}$ alkanoyloxy, $C_{1-6}$ alkanoylamino, amino or p-guanidino.

Suitable optional substituents for acryloyl blocking groups include $C_{1-6}$ alkyl, furyl, phenyl or $C_{1-6}$ alkylphenyl.

Examples of a removable blocking groups include p-anisoyl and N,N-dimethyl 4-amino benzoyl.

Blocking of the active center with a removable blocking group can be effected by methods described in European Patent No. 0009879.

The above mentioned derivatives of the degraded species of t-PA may be used in any of the methods and compositions described hereinafter for the t-PA species itself.

Our results indicate that a recognition site determining rapid clearance of the native t-PA molecule resides on the fragment which is absent in the degraded species of the invention. Once this putative site has been removed, the active center of the molecule appears to be recognised by another clearance mechanism. Hence blocking of the active center improves pharmacokinetic properties markedly.

The t-PA species of the invention is suitably administered in the form of a pharmaceutical composition.

Accordingly the present invention also provides a pharmaceutical composition comprising a fibrinolytically active degraded species of t-PA or derivative thereof as herein defined in combination with a pharmaceutically acceptable carrier.

The compositions according to the invention may be formulated in accordance with routine procedures as pharmaceutical compositions adapted for intravenous administration to human beings.

Typically compositions for intravenous administration are solutions of the sterile enzyme in sterile isotonic aqueous buffer. Where necessary the composition may also include a solubilising agent to keep the degraded t-PA species in solution and a local anaesthetic such as lignocaine to ease pain at the site of injection. Generally, the t-PA species of the invention will be supplied in unit dosage form for example as a dry powder or water free concentrate in a hermetically sealed container such as an ampoule or sachette indicating the quantity of protein in activity units. Where the t-PA species includes a removable blocking group an indication of the time within which the free protein will be liberated may be given. Where the protein is to be administered by infusion, it will be dispensed with an infusion bottle containing sterile pharmaceutical grade 'Water for Injection' or saline. Where the protein is to be administered by injection, it is dispensed with an ampoule of sterile water or saline. The injectable or infusable composition will be made up by mixing the ingredients prior to administration.

The quantity of material administered will depend upon the amount of fibrinolysis required and the speed with which it is required, the seriousness of the thromboembolic condition and position and size of the clot. The precise dose to be employed and mode of administration must per force in view of the nature of the complaint be decided according to the circumstances by the physician supervising treatment. However, in general, a patient being treated for a mature thrombus will generally receive a daily dose of from 0.01 to 10 mg/kg of body weight either by injection in for example up to five doses or by infusion.

Within the above indicated dosage range, no adverse toxicological effects are indicated with the compounds of the invention.

Accordingly, in a further aspect of the invention there is provided a method of treating thrombotic diseases, which comprises administering to the sufferer an effective non-toxic amount of a fibrinolytically active degraded species of t-PA or derivative thereof as herein defined.

The invention further provides a fibrinolytically active degraded species of t-PA or derivative thereof as herein defined, for use as an active therapeutic substance and, in particular, for use in the treatment of thrombotic diseases.

The following Examples illustrate the invention.

The molecular weights ($M_r$) referred to herein are apparent molecular weights as determined by sodium dodecylsulphate polyacrylamide gel electrophoresis under non-reducing conditions.

EXAMPLE 1

Isolation of alanine$_{160}$ t-PA ($M_r$=38,000)

Tissue-type plasminogen activator secreted into serum-free media by recombinant Bowes melanoma cells was shown by SDS PAGE (Laemmli, U.K., 1970, Nature, 227, 680-682) followed by fibrin zymography (Granelli-Piperno, A. and Reich, E., 1978, J. Exp. Med., 148, 223-234) to contain several species of t-PA. All the t-PA species were purified by chromatography on zinc chelate and lysine Sepharose* (Browne, M. J. et al, 1985, Gene, 33, 279) and concentrated by ultrafiltration. The concentrate was buffer-exchanged into 0.05 M NH$_4$HCO$_3$ and lyophilised. The t-PA species were separated by chromatography of the reconstituted lyophilisate through a column of Sephadex G-75*. Fractions containing the $M_r$=approx. 38,000 species were identified using the chromogenic substrate H-D-ile-pro-arg p-nitroanilide. HCl or by SDS PAGE followed by fibrin zymography. These fractions were pooled, concentrated by ultrafiltration and rechromatographed on the column of Sephadex G-75. The fractions containing the $M_r$=approx. 38,000 t-PA species were identified as before, pooled, concentrated by ultrafiltration and buffer-exchanged into a suitable buffer for lyophilisation or for direct use in vivo.
* Sepharose and Sephadex are trademarks The product was characterised as a $M_r$=approx. 38,000 t-PA because (1) it bears immunological resemblance to t-PA and to t-PA B-chain and is immunologically distinct from u-PA, (2) by SDS PAGE under non-reducing conditions it has a $M_r$=approx. 38,000 both by staining for protein using PAGE Blue 83 (British Drug Houses, U.K.) or by fibrin zymography (FIG. 1), (3) the dose response on human fibrin plates is parallel to that of $M_r$=63,000/65,000 t-PA and is not parallel to that of u-PA and (4) the molecule has significant fibrin binding activity in a purified human fibrin clot assay in which u-PA does not bind—see Example 4.

EXAMPLE 2

Isolation of partially-purified alanine$_{160}$t-PA ($M_r$=40,000)

During routine purifications of t-PA using zinc chelate and lysine Sepharose (as described in Example 1) a small but variable proportion of the recovered t-PA activity is always in the non-adsorbed fraction ($V_o$) of the lysine Sepharose column. When analysed by SDS PAGE followed by fibrin zymography a t-PA-like species of apparent $M_r$40,000 is detected in these preparations. This material, when rechromatographed on a fresh lysine Sepharose column, will adsorb to it and can be dissociated subsequently using 0.02 M Tris/0.5 M NaCl/0.5 M L-arginine/0.01% Tween 80 pH 7.4. After concentration by ultrafiltration, partial separation of the activator species present can be achieved by a single passage through a column of Sephadex G75. The fractionated eluate of the column was analysed by SDS PAGE/fibrin zymography and the fractions enriched in the $M_r$=40,000 species were pooled and concentrated. Analysis by fibrin zymography showed a clear distinction between the $M_r$=40,000 species and the $M_r$=38,000 species of Example 1 (FIG. 1).

EXAMPLE 3

Demonstration of purity of alanine$_{160}$t-PA ($M_r$=38,000)

The high purity of the preparation of alanine$_{160}$-PA ($M_r$=38,000) described in Example 1 was demonstrated by the following tests:

(1) After SDS PAGE followed by protein staining the non-reduced sample showed a single major band at $M_r$=38,000.

(2) N-terminal sequence analysis carried out by Sequal Ltd., Aberdeen, U.K., gave an N-terminal sequence for the A-chain part of the molecule of "alanine-glycine-lysine-tyrosine-". Contaminating proteins would have prevented the identification of these residues.

(3) After SDS PAGE followed by fibrin zymography a single lysis zone was present (FIG. 1).

EXAMPLE 4

Demonstration of fibrin-binding of alanine$_{160}$t-PA

The fibrin-binding test employed was similar to that of Rijken, D. C. and Collen, D. (J. Biol. Chem. (1981) 256, 7035). Essentially plasminogen activator-containing fibrinogen solution was treated with or without thrombin and any precipitable material (e.g. fibrin) isolated by centrifugation. The supernatants were assayed using a fibrin plate assay (as described in Example 7). The difference in activator concentration between the supernatants of the two treatments (with or without thrombin) was equivalent to the amount of material adsorbed to the clot.

Using an initial fibrinogen (Kabi, Grade L) concentration of 1.5 mg/ml and four concentrations of alanine$_{160}$t-PA in the range approx. 100 to 10 IU/ml the amount of alanine$_{160}$t-PA adsorbed to the fibrin clot was 55 per cent of the amount in the original solution.

EXAMPLE 5

Synthesis of N'N'dimethyl 4-aminobenzoyl alanine$_{160}$t-PA (M$_4$=38,000)

5.5 nmoles alanine$_{160}$t-PA (140 µg/ml) in 0.02 M phosphate, 0.15 M sodium chloride, 0.01% Tween 80 pH 7.4 (PBS/TW) was treated with a 3-fold molar excess of N'N'dimethyl 4-aminobenzoic acid 4-amidinophenyl ester. HCl at 25° C. for 30 min. Free acylating agent was then removed by buffer-exchange into PBS/TW using Sephadex G-25 and the product stored at −70° C*.

Deacylation studies carried out in 0.1 M Tris, 0.15 M sodium chloride, 20% (v/v) glycerol, 0.01% Tween 80 pH 7.4$^{37°}$ gave a deacylation rate constant of $3.4 \times 10^{-4}$ sec$^{-1}$ (mean of two determinations).
* The method used for the synthesis was similar to that described in European Patent No. 0009879.

EXAMPLE 6

Synthesis of p'-anisoyl alanine$_{160}$t-PA 21 nmoles alanine$_{160}$t-PA (0.5 mg/ml) in phosphate buffered saline (PBS 'A'; Dulbecco)/0.01% Tween 80/0.025 M L-lysine/ 10 mg/ml mannitol/ 1 mM E-aminocaproate (EACA) was treated with a 3-fold molar excess of p-amidinophenyl p'-anisate.HCl at 25° C. for 30 min. Free acylating agent was removed by buffer-exchange into PBS 'A'/ 0.01% Tween 80/0.02 M EACA, using Sephadex G25. The product was stored at −70° C.

Deacylation studies carried out in PBS 'A'/0.01% Tween 80 gave a deacylation rate constant of $3.9 \times 10^{-4}$ 80 sec$^{-1}$. Prior to deacylation at least 93 per cent of the material was in the acyl form.

EXAMPLE 7

Assay of fibrinolytic activity in the bloodstream of guinea pigs

Male Dunkin Hartley guinea pigs (350–450 g) were anaesthetized with urethane (25% w/v solution; 6 ml/kg i.p.). One carotid artery was cannulated for collection of blood samples. One femoral vein was cannulated for injection of heparin (50 U/kg i.v.) and compound under test. Approximately 5 min after heparinization, a pre-dose blood sample was taken and mixed with 0.1 volumes 129 mM trisodium citrate. The compound under test was then injected (1 ml/kg) over 10s. Further blood samples were taken exactly 2, 4, 8, 16, 30 and 60 min later. Heparin treatment (50 U/kg i.v.) was repeated after the 30 min sample to maintain cannula patency All citrated blood samples were kept on ice until the end of each experiment, then centrifuged at 1700 g for 15 min at 4° C. to obtain plasma. The euglobulin fraction was precipitated by adding 0.1 ml of each plasma to 1.82 ml ice-cold 0.011% (v/v) acetic acid in water. After 30 min standing in ice, all tubes were centrifuged at 1700 g for 15 min at 4° C. The supernatants were poured away, the inner walls of each tube carefully wiped dry and each precipitate redissolved in 0.4 ml phosphate-buffered saline, pH 7.4, containing 0.01% (v/v) Tween 80. Aliquots (30 ul) were then applied to fibrin plates in quadruplicate. Fibrin plates were prepared from 0.4% (w/v) human fibrinogen (Kabi, Grade L, Flow Laboratories, Scotland) dissolved in 0.029 M barbitone in 125 mM NaCl, pH 7.4, pipetted (10 ml) into 10×10 cm square plastic dishes (Sterilin) and clotted by rapid mixing with 0.3 ml bovine thrombin (50 NIH units/ml, Parke-Davis, U.K.). Plates were incubated at 37° C. for 18-24h usually, but longer if required, and stained with aqueous bromophenol blue. For each lysis zone, two diameters perpendicular to each other were measured using Vernier callipers. All diameters for each sample were averaged, and this mean converted to fibrinolytic activity by reference to a calibration curve. The latter was obtained by adding known amounts of the compound under test to the pre-dose plasma of each animal. These standards were processed using the same method and at the same time as the experimental samples. To construct the calibration curve, diameters (mm) were plotted against log$_{10}$ concentration of compound. The plasma concentration of compound in each experimental sample was expressed as a percentage of that expected on the assumption of 50 ml plasma/kg body weight for each guinea pig.

Figure 2:
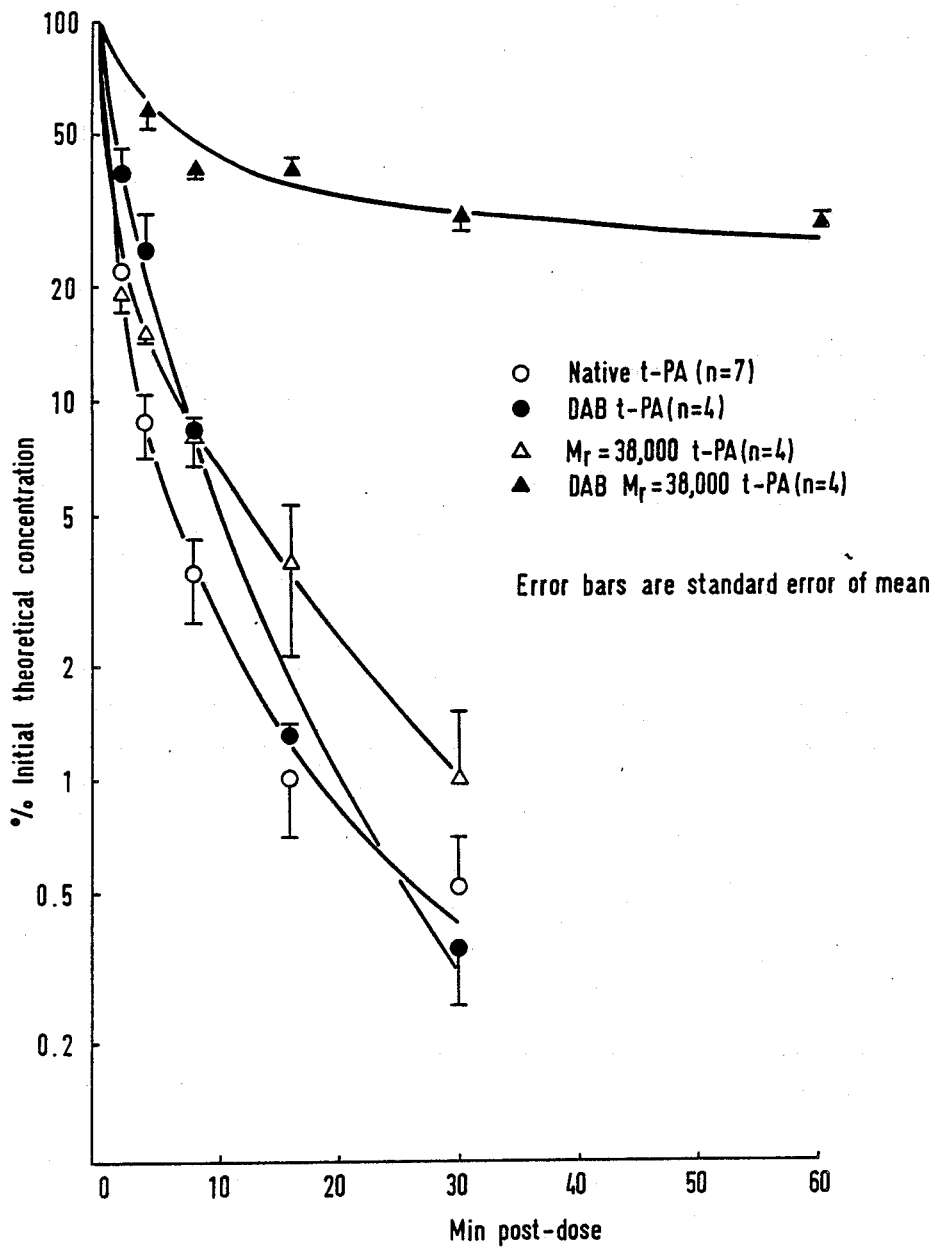

FIG. 2 shows that the N'N'-dimethyl 4-aminobenzoyl (DAB) derivative of the $M_r = 38,000$ species of t-PA is cleared significantly more slowly from the circulation of the guinea pig than is either t-PA or the DAB-derivative of t-PA.

In the figures:

FIG. 1: Sodium dodecylsulphate polyacrylamide gel electrophoresis followed by fibrin zymography of the two variants of alanine$_{160}$t-PA Highly purified ala$_{160}$t-PA ($M_r = 38,000$) [lane A] or partially-purified ala$_{160}$t-PA ($M_r = 40,000$) [lane B] or a mixture of both [lane C] were analysed by SDS PAGE followed by fibrin zymography essentially as described in Example 1. Fibrinolytically-active species in the preparations appear as clear lysis zones against the unlysed fibrin background. Lane D is fibrinolytic marker proteins.

FIG. 2: Fibrinolytic activity in the bloodstream of guinea pigs.

In the plot of % Initial theoretical concentration against minutes post dose, the plot symbols are as follows:

○ Native t-PA (n=7)
● DAB t-PA (n=4)
△ $M_r = 38,000$ t-PA (n=4)
▲ DAB $M_r = 38,000$ t-PA (n=4)
n = number of animals
Error bars are standard error of mean.

I claim:

1. A purified fibrinolytically active degraded species of human tissue-type plasminogen activator comprising a fibrinolytically intact B chain of native human t-PA linked to kringle 2 as the only functionally and structurally intact domain of native human t-PA A chain.

2. A species according to claim 1 having a molecular weight in the region of 38,000–40,000.

3. A species according to claim 2 having a molecular weight of around 38,000.

4. A species according to claim 1, of at least 70% purity.

5. A purified fibrinolytically active degraded species of human tissue-type plasminogen activator, consisting essentially of purified alanine$_{160}$t-PA.

* * * * *